United States Patent [19]

Bruzzese et al.

[11] 4,251,520

[45] Feb. 17, 1981

[54] GLUCOFURANOSE DERIVATIVES

[76] Inventors: Tiberio Bruzzese, Via Frua 21/6; Lorenzo Ferrari, Via Biella 8; Aurelio F. Notarianni, Via dei Frassini 6, all of Milan, Italy

[21] Appl. No.: 79,942

[22] Filed: Sep. 26, 1979

Related U.S. Application Data

[63] Continuation-in-part of Ser. No. 963,263, Nov. 24, 1978, abandoned, which is a continuation of Ser. No. 852,047, Nov. 16, 1977, abandoned.

[30] Foreign Application Priority Data

Nov. 16, 1976 [GB] United Kingdom ............... 47662/76

[51] Int. Cl.³ ....................... A61K 31/70; C07H 15/04
[52] U.S. Cl. ......................................... 424/180; 536/4; 536/120

[58] Field of Search ..................... 536/4, 120; 424/180

[56] References Cited

U.S. PATENT DOCUMENTS

| 3,939,145 | 2/1976 | Gordon | 536/4 |
| 3,939,146 | 2/1976 | Gordon | 536/4 |
| 4,056,322 | 1/1977 | Gordon et al. | 536/4 |

*Primary Examiner*—Johnnie R. Brown
*Assistant Examiner*—Blondel Hazel
*Attorney, Agent, or Firm*—Wenderoth, Lind & Ponack

[57] ABSTRACT

The present invention provides a method of treating inflammatory and pyretic conditions in mammals, including humans, which comprises administering a derivative of 1,2:5,6-di-O-isopropylidene-α-D-glucofuranose to a mammal requiring treatment for an inflammatory or pyretic condition.

1 Claim, No Drawings

GLUCOFURANOSE DERIVATIVES

This application is a continuation-in-part of application Ser. No. 963,263, filed Nov. 24, 1978 (now abandoned), which application is a continuation of application Ser. No. 852,047, filed Nov. 16, 1977 (now abandoned).

BACKGROUND OF THE INVENTION

Over the past few years, research on non-acidic substances with an anti-inflammatory activity have increased. Of these, a few derivatives related structurally to the glucides have proved to be particularly interesting.

They normally exert a venotropic action and inhibit the effects of antigen-antibody reaction. A stimulating action on fibrinolytic activity has also been observed both in vitro and in vivo. A compound in this class which has been studied in some detail is tribenoside or ethyl-3,5,6-tri-O-benzyl-D-glucofuranoside (Glyvenol).

Interest in this class of compounds is not only associated with effective therapeutic activity but also with their innocuity at a gastric and general level. It is known that steroid and non-steroid anti-inflammatory agents give rise to very considerable side effects and, because of this, their use must often be discontinued or suspended or the dose reduced, thus seriously prejudicing the final therapeutic result. Phenylbutazone, acetylsalicylates and cortisones give rise to ulcerogenic effects of different intensity, even causing haemorrhagic manifestations which can be fatal; non-steroid anti-inflammatory agents can produce hepatotoxic manifestations, involving an immunitary mechanism of hypersensibilisation, with icteric-type manifestations or fatty degeneration. Some non-steroid anti-inflammatory agents, such as phenylbutazone, have been described as being nephrotoxic and they can give rise to neuropsychic disturbances and either sensory symptoms or allergic reactions at a cutaneous and staminal cell level.

Therefore, interest in atoxic anti-inflammatory agents is more than justified, bearing in mind that anti-inflammatory therapy is generally carried out on a medium or long-term basis.

Of the derivatives structurally related to the glucides, the best known is the above-mentioned ethyl 3,5,6-tri-O-benzyl-D-glucofuranoside (Glyvenol):

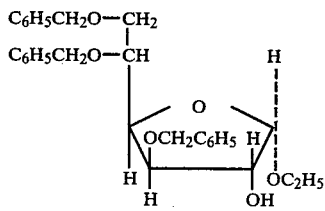
(I)

This is a compound with anti-inflammatory and anti-allergic activity which is used in the treatment of venous disorders in order to reduce the permeability of blood vessel walls and to inhibit exudative processes.

Considering the novelty of its structure, we have investigated whether a pharmacological activity can even be found in similar but novel compounds.

Beginning, therefore, with D-glucose, we have prepared 1,2:5,6-di-O-isopropylidene-α-D-glucofuranose (II):

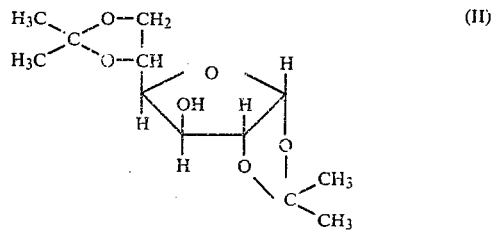
(II)

as well as 1,2-O-isopropylidene-α-D-glucofuranose and 1,2-O-isopropylidene-3,5,6-tri-O-benzyl-α-D-glucofuranose (1; Glen W. L., Myers G. S., Grant G. A., J. Chem. Soc., 2568/1951; (2) Meyer A. S., Reichstein T., Helv. Chim. Acta, 29, 139/1946; (3) Huber G., Rossi A., Helv. Chim. Acta, 51, 1185/1968) and have compared these compounds with (I) for anti-inflammatory activity against carrageenin-induced oedema (500 mg/kg, p.o. in rats).

Preliminary tests showed, surprisingly, that (II) has an activity which is fully comparable with that of (I). Therefore, we have prepared a number of 3-O-derivatives in order to obtain even more potent compounds.

SUMMARY OF THE INVENTION

Thus, according to the present invention, there is provided a method of treating inflammatory and pyretic conditions in mammals, including humans, which comprises administering a compound of the formula:

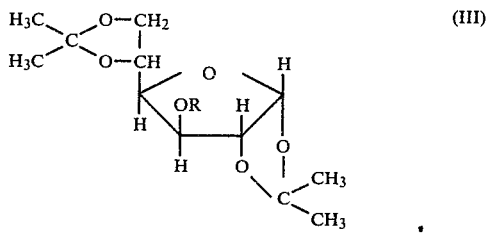
(III)

wherein R is a straight-chained or branched alkyl radical containing at least 5 carbon atoms or an alkenyl radical containing at least 4 carbon atoms or an alkynyl radical or an acyloxy radical or an alkoxy radical or a carboxyalkyl radical or a radical of the general formula

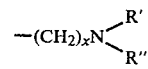

in which x is a whole number and R' and R", which may be the same or different, are hydrogen atoms or alkyl radicals or in which R' and R", together with the nitrogen atom to which they are attached, form a heterocyclic ring which can contain an additional heteroatom; or an acid-addition salt thereof when (III) is a basic compound, to a mammal requiring treatment for an inflammatory or pyretic condition.

DETAILED DESCRIPTION OF THE INVENTION

In general formula (III), the alkynyl, acyloxy, alkoxy and carboxyalkyl radicals preferably contain up to 6 carbon atoms and the alkyl radicals R' and R" preferably also contain up to 6 carbon atoms. When R' and R", together with the nitrogen atom to which they are attached, form a heterocyclic ring, this ring may additionally contain an oxygen, sulphur or second nitrogen heteroatom. Furthermore, x is preferably a whole number of up to 5.

In order to prepare the 3-O-substituted compounds (III), the compound (II) can be converted into the corresponding sodium salt and then reacted with an appropriate reagent in the usual manner [(1); (4) Shyluk W. P., Timell T. E., Can. J. Chem., 34, 575/1956]. Some of the compounds obtained have already been reported in literature but none of them has been evaluated for their biological activity.

Pharmacological tests were carried out to evaluate the acute toxicity, anti-inflammatory and capillary permeability action, antipyretic, analgesic and anti-spasmodic in vitro action. Compound (I) was used as a reference compound, together with aspirin and phenylbutazone.

The compounds which have been prepared are summarised in Table 1, together with their physico-chemical characteristics, the method of synthesis and the yields obtained.

TABLE I

3-O-derivatives of 1,2:5,6-di-O-isopropylidene-α-D-glucofuranose

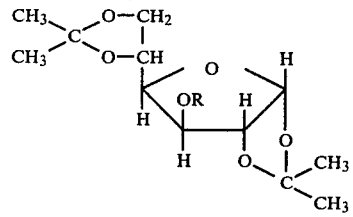

| Compound No. | R | M.W. | Molecular formula[a] | Method of synthesis |
|---|---|---|---|---|
| II | H | 260.28 | $C_{12}H_{20}O_6$ | |
| III | $CH_3$ | 274.31 | $C_{13}H_{22}O_6$ | |
| IV | $CH_2CH_3$ | 288.33 | $C_{14}H_{24}O_6$ | |
| V | $(CH_2)_2CH_3$ | 302.36 | $C_{15}H_{26}O_6$ | |
| VI | $(CH_2)_3CH_3$ | 316.38 | $C_{16}H_{28}O_6$ | |
| VII | $(CH_2)_4CH_3$ | 330.41 | $C_{17}H_{30}O_6$ | A |
| VIII | $(CH_2)_{15}CH_3$ | 484.70 | $C_{28}H_{52}O_6$ | A |
| IX | $CH_2CH=CH_2$ | 300.34 | $C_{15}H_{24}O_6$ | |
| X | $CH_2C\equiv CH$ | 298.33 | $C_{15}H_{22}O_6$ | A |
| XI | $CH_2C_6H_5$ | 350.40 | $C_{19}H_{26}O_6$ | |
| XII | $COCH_3$ | 302.32 | $C_{14}H_{22}O_7$ | D |
| XIII | $CH_2COOH$ | 318.32 | $C_{14}H_{22}O_8$ | C |
| XIV | $(CH_2)_2N(CH_3)_2$ | 331.40 | $C_{16}H_{29}NO_6$ | B |
| XV | $(CH_2)_2N(CH_2CH_3)_2$ | 359.45 | $C_{18}H_{33}NO_6$ | |
| XVI | $(CH_2)_2N[(CH_2)_2CH_3]_2$ | 387.50 | $C_{20}H_{37}NO_6$ | B |
| XVII | $(CH_2)_2N[CH(CH_3)_2]_2$ | 387.50 | $C_{20}H_{37}NO_6$ | B |
| XVIII | $(CH_2)_2N\langle\rangle$ (pyrrolidine) | 357.44 | $C_{18}H_{31}NO_6$ | B |
| XIX | $(CH_2)_2N\langle\rangle$ (piperidine) | 371.46 | $C_{19}H_{33}NO_6$ | B |
| XX | $(CH_2)_2N\langle\rangle O$ (morpholine) | 373.44 | $C_{18}H_{31}NO_7$ | B |
| XXI | $(CH_2)_2N(CH_2C_6H_5)_2$ | 483.58 | $C_{28}H_{37}NO_6$ | B |
| XXII | $(CH_2)_3N(CH_3)_2$ | 345.43 | $C_{17}H_{31}NO_6$ | B |

[a]All compounds were analysed for C and H; basic derivatives were also analysed for N and were within ± 0.4% of theoretical values.

| Compound No. | Yield % | Lit. ref. | b.p. (mm) or m.p., °C.[b] | $n_D^{20}$ | $[α]_D^{20(c)}$ | $R_f^{(d)}$ |
|---|---|---|---|---|---|---|
| II | | 1 | 109[e] | — | −11 | 0.16 (1) / 0.90 (2) |
| III | | 1 | 77–80 (0.2) | 1.4560 | −30.3 | 0.51 (1) |
| (IV) | | 1 | 95–96 (0.3) | 1.4517 | −27.9 | 0.60 (1) |
| (V) | | 1 | 100–102(0.25) | 1.4495 | −26.9 | 0.70 (1) |
| (VI) | | 1 | 120–123(1.0) | 1.4492 | −25.5 | 0.72 (1) |
| (VII) | 70 | | 112–114(0.25) | 1.4504 | −24.3 | 0.74 (1) |
| (VIII) | 44 | | 180–182(0.25) | 1.4583 | −14.7 | 0.78 (1) |
| (IX) | | (5) | 115–118(0.2) | 1.4608 | −22 | 0.62 (1) |
| (X) | 60 | | 120–125(0.5) | 1.4707 | −12.6 | 0.57 (1) |
| (XI) | | (6) | 123–126(0.25) | 1.4985 | −24.8 | 0.63 (1) |
| (XII) | 82 | | 50–52[f] | — | −28.5 | 0.40 (1) |
| (XIII) | 75 | | [g] | 1.4592 | −19.7[h] | 0 (1 and |

TABLE I-continued

3-O-derivatives of 1,2:5,6-di-O-isopropylidene-α-D-glucofuranose $$\begin{array}{c}\text{CH}_3\diagdown\phantom{C}\diagup\text{O}-\text{CH}_2\\\phantom{CH_3}C\phantom{O-CH}|\\\text{CH}_3\diagup\phantom{C}\diagdown\text{O}-\text{CH}\end{array}$$

(structure of 1,2:5,6-di-O-isopropylidene-α-D-glucofuranose with OR at 3-position)

| | | | | | 2) |
|---|---|---|---|---|---|
| (XIV) | 65 | | 114–116(0.25) | 1.4584 | −27.6 | 0.37 (2) |
| (XV) | | (7) | 120–122(0.25) | 1.4597 | −24.8 | 0.43 (2) |
| (XVI) | 72 | | 132–134(0.5) | 1.4504 | −22.5 | 0.48 (2) |
| (XVII) | 78 | | 136–137(0.25) | 1.4591 | −21.1 | 0.68 (2) |
| (XVIII) | 66 | | 135–136(0.25) | 1.4711 | −26.1 | 0.46 (2) |
| (XIX) | 68 | | 134–136(0.5) | 1.4739 | −26 | 0.50 (2) |
| (XX) | 73 | | 150–153(0.2) | 1.4742 | −24.2 | 0.86 (2) |
| (XXI) | 57 | | 180–182(0.2) | 1.5251 | −18 | 0.59 (1) |
| (XXII) | 50 | | 115–117(0.2) | 1.4580 | −28 | 0.42 (2) |

[b] Boiling and melting points are uncorrected
[c] At 2% concentration in ethanol
[d] Thin layer chromatography on Merck 60 $F_{254}$ strips, solvent system No. 1: diisopropyl ether - ligroin (70:30 v/v); No.2: chloroform - methanol -acetic acid (85:14:1 v/v); detection: iodine vapour
[e] Recrystallised from ligroin (b.p. 80°–120° C.)
[f] Recrystallised from petroleum ether (b.p. 40°–60° C.)
[g] The product could not be distilled without decomposition
[h] At 2% concentration in ethanol:chloroform (1:1 v/v)
[5] Hoiness D.E. et al., Can.J.Chem., 46, 667/1968
[6] Iwashige T. et al., Chem.Pharm.Bull., 15, 1803/1967
[7] Roberts E.J. et al., Can.J.Chem., 45, 261/1967.

The compounds can be prepared according to one of the following 4 methods:

Method A 3-n-Pentyl-1,2:5,6-di-O-isopropylidene-α-D-glucofuranose (VII)

6 g (0.25 mol) sodium hydride were added portionwise, while stirring, to a solution of 26 g (0.1 mol) 1,2:5,6-di-O-isopropylidene-α-D-glucofuranose in 200 ml. anhydrous toluene. The reaction mixture was heated under gentle reflux for 1.5 hours, then 45 g. (0.3 mol) 1-bromopentane were added dropwise, whereafter the reaction mixture was further heated for 24 hours. Since chromatographic control showed that some of the starting material had not reacted, an additional 6 g. sodium hydride and 45 g. 1-bromopentane were added and the reaction mixture refluxed for a further 48 hours. After cooling, the suspension was carefully treated with water and the toluene layer was separated, dried with anhydrous sodium sulphate and evaporated to dryness under reduced pressure. The residue was mixed with petroleum ether (b.p. 40°–60° C.), any insoluble matter being discarded, and the solution was then evaporated to dryness. The oily residue was distilled in a vacuum to give (VII), in the form of a colourless oil; b.p. 112°–114° C./0.25 mm.Hg.

Method B 3-(2-Dimethylaminoethyl)-1,2:5,6-di-O-isopropylidene-α-D-glucofuranose (XIV)

24 g. (0.5 mol) sodium hydride (50% dispersion in oil) were added portionwise, while stirring, to a solution of 52 g. (0.2 mol) 1,2:5,6-di-O-isopropylidene-α-D-glucofuranose in 300 ml. anhydrous toluene. The reaction mixture was gently refluxed for 1.5 hours and then a solution of 64.5 g. (0.6 mol) 1-chloro-2-dimethylaminoethane in 200 ml. anhydrous toluene was added dropwise. After boiling for 48 hours, the reaction mixture was cooled, washed with water and extracted with diluted hydrochloric acid. The acid extract was washed with toluene, treated with a dilute aqueous solution of sodium hydroxide until moderately alkaline and the oil which separated was extracted with diethyl ether.

After drying the ethereal extract, the solvent was evaporated and the residue was purified by distillation to give (XIV) in the form of an almost colourless oil; b.p. 114°–116° C./0.25 mm. Hg.

Method C

3-Carboxymethyl-1,2:5,6-di-O-isopropylidene-α-D-glucofuranose (XIII)

A solution of 26 g. (0.1 mol) 1,2:5,6-di-O-isopropylidene-α-D-glucofuranose in 200 ml. dioxan was treated with 12 g. (0.25 mol) sodium hydride (50% dispersion in oil) as in the preceding Example, whereafter 32.2 g. (0.3 mol) sodium chloroacetate were added and the reaction mixture then refluxed for 24 hours. The solvent was then removed in a vacuum and the residue was extracted, while cooling, with dilute aqueous sodium hydroxide solution, whereafter the aqueous solution was washed with chloroform and acidified and the product which separated was extracted with chloroform. After drying, the solvent was distilled off to give (XIII) in the form of a viscous oil which could not be distilled without decomposition.

Method D

3-Acetyl-1,2:5,6-di-O-isopropylidene-α-D-glucofuranose (XII)

100 g. acetic anhydride were added to a solution of 26 g. (0.1 mol) 1,2:5,6-di-O-isopropylidene-α-D-glucofuranose in 200 ml. pyridine and the reaction mixture then stirred overnight at ambient temperature, whereafter it was evaporated to dryness under reduced pressure and temperature. The residue was dissolved in diethyl ether, the ethereal solution was thoroughly washed with water and dried and the solvent was distilled off. The remaining oil solidified upon standing to give (XII), which was crystallised from petroleum ether (b.p. 40°–60° C.) to give colourless crystals; m.p. 50°–52° C.

The results of the pharmacological tests are summarised in the following Table 2. By the oral route, all the compounds had a low toxicity, some of them (VIII, IX, XI–XII and reference compound I) being well tolerated even at a dose of 4,000 mg./kg.

TABLE 2

| Compound No. | Approx. LD$_{50}$ (mouse) mg/kg p.o. | Anti-inflammatory activity | | | |
|---|---|---|---|---|---|
| | | 500 mg/kg p.o. rat % inhibition of edema induced by | | | 200 mg/kg p.o. rat % inhibition of granuloma |
| | | carrageenan | dextran | formalin | |
| II | 4000 | 33 | 0 | 19 | 0 |
| III | 2000 | 51 | 35 | 25 | 0 |
| IV | 2000 | 37 | 14 | 33 | |
| V | 1000 | 28 | 0 | 0 | |
| VI | 3000 | 33 | 13 | 24 | |
| VII | 4000 | 62 | 31 | 48 | 19 |
| VIII | >4000 | 13 | 0 | 0 | |
| IX | >4000 | 68 | 39 | 29 | 16 |
| X | 1500 | 53 | 65 | 36 | 0 |
| XI | >4000 | 39 | 0 | 21 | |
| XII | >4000 | 21 | 0 | 9 | |
| XIII | >4000 | 10 | 4 | 18 | |
| XIV | 1500 | 62 | 54 | 28 | 0 |
| XV | 3000 | 60 | 58 | 4 | 0 |
| XVI | 750 | 23 | 41 | 24 | 0 |
| XVII | 1000 | 73 | 35 | 32 | 0 |
| XVIII | 1500 | 68 | 64 | 38 | 0 |
| XIX | >1000 | 64 | 56 | 28 | |
| XX | 1500 | 59 | 65 | 43 | 0 |
| XXI | >2000 | 29 | 17 | 19 | |
| XXII | 2000 | 39 | 59 | 37 | 0 |
| Aspirin | 1000 | 53 | 47 | 29 | 12 |
| Phenylbutazone | 1000 | 52$^e$ | 15$^e$ | 13$^e$ | 31 |
| I | >4000 | 20 | 0 | 14 | 0 |

| | Capillary permeability (500 mg/kg p.o. mouse) Decrease % | Antipyretic activity (400 mg/kg p.o. rat) %$^a$ | Analgesic activity (500 mg/kg p.o. mouse)$^b$ | | Antispasmodic activity in vitro, ED$_{50}$ (γ/ml) Inhib. of spasm by | |
|---|---|---|---|---|---|---|
| | | | Increase of reaction time %$^c$ | Protection from writhing % | histamine | acetylcholine |
| | 46 | 63 | 0 | 20 | >100 | >100 |
| | 37 | 70 | 20 | 20 | 100 | >100 |
| | 42 | 31 | 30 | 0 | 150 | >100 |
| | 53 | 37 | 10 | 20 | >100 | >100 |
| | 57 | 51 | 40 | 0 | >100 | >100 |
| | 4 | 0 | 0 | 20 | >100 | >100 |
| | 22 | 0 | 0 | 20 | | |
| | 43 | 44 | 0 | 20 | 60 | 60 |
| | 107 | 0 | 0 | 20 | 50 | 50 |
| | 29 | 8 | 0 | 20 | >100 | >100 |
| | 26 | 0 | 20 | 0 | >100 | >100 |
| | 14 | 5 | 0 | 0 | >100 | >100 |
| | 35 | 43 | 10 | 20 | 100 | >100 |
| | 20 | 8 | 10 | 0 | 100 | >100 |
| | | 29 | 0 | 0 | 12 | 100 |

TABLE 2-continued

| | | | | | |
|---|---|---|---|---|---|
| 32 | 15 | 0 | 40 | 70 | 100 |
| 50 | 0 | 10 | 0 | 100 | >100 |
| 17 | 55 | | | | |
| 58 | 14 | 40 | 0 | >100 | >100 |
| | 25 | 0 | 60 | | |
| 26 | 30 | 10 | 20 | 6 | 100 |
| 73$^d$ | 100 | 70 | 100 | >100 | >100 |
| 75$^d$ | 85 | 10 | 100 | >100 | >100 |
| 48 | 9 | 10 | 0 | 20 | 30 |

$^a$Activity expressed as potency in comparison with aspirin = 100
$^b$Compounds and standards were inactive with tail pinch test
$^c$Hot plate test
$^d$At a dose of 400 mg/kg p.o.
$^e$At a dose of 200 mg/kg p.o.

The anti-inflammatory activity tests showed that all the tested 3-O-substituted 1,2:5,6di-O-isopropylidene-α-D-glucofuranose compounds have a good activity and, in particular, some saturated (III, VII) and unsaturated (IX, X) alkyl derivatives and the basic derivatives in general (XIV–XXII) were clearly more active than (I) in inhibiting oedema induced by carrageenin, dextran and formalin and are as potent as or more potent than aspirin and phenylbutazone.

Among the compounds tested, (VII) and (IX) also showed some inhibitory activity in the granuloma cotton pellet test.

The capillary permeability test, which is one of the best tests for demonstrating the action typical of the reference compound (I), showed the same degree of activity for several of the new test compounds without evident correlation with the structure of the R-substituent. However, the reduction of the permeability obtained was lower than that obtained with aspirin and phenylbutazone.

Another characteristic activity common to most of the compounds to be used according to the present invention is the antipyretic action, which is also present in the parent compound (II) not substituted in the 3-position, and is retained in some of the short-chain, saturated (III, VI) and unsaturated (IX, X) alkyl derivatives, and in some of the basic derivatives (XIV, XIX). This activity was generally lower than in the case of the reference compounds aspirin and phenylbutazone but much higher than in the case of (I), which had little or no activity.

The analgesic action was, in all cases, moderate or nil, in analogy with reference compound (I).

The antispasmodic activity tests in vitro demonstrated that (XVI) and (XXII) inhibited spasms induced by histamine at relatively low concentrations, whilst the unsaturated derivatives (IX) and (X) were also moderately active against spasms produced by acetylcholine. The potency of the action was comparable to that of (I), whilst aspirin and phenylbutazone were inactive.

In conclusion, the pharmacological results obtained verify that 1,2:5,6-di-O-isopropylidene-α-D-glycofuranose and the 3-O-substituted derivatives thereof constitute a new class of compounds which have a notable anti-inflammatory and antipyretic action, are able to decrease the permeability of venous walls and, in some cases, have an antagonistic action with regard to biogenous amines.

These activities are of interest pharmacologically and practically, especially when considering that some of the compounds also have a very low toxicity. In comparison with the reference compound (I), some compounds, for example 3-O-allyl-1,2:5,6-di-O-isopropylidene-α-D-glucofuranose (IX), demonstrate, in this preliminary pharmacological screening, an analogous or even better spectrum and potency of action.

The compounds used according to the present invention can be administered in admixture with a solid, liquid or semi-liquid pharmaceutical diluent or carrier.

Compositions which can be used in carrying out the method according to the present invention include gelatine capsules and, after admixture with an appropriate carrier, tablets, effervescent tablets, dragees, capsules, powders, emulsions, oily solutions and syrups for oral administration, as well as suppositories, injection solutions and ointments or tinctures for topical use, which are convenient in cases of local inflammation in humans and mammals. In all cases, the active compounds are diluted with an appropriate amount of a pharmaceutically acceptable solid or liquid vehicle, optionally in association with other active materials, for example vitamins.

Typical dosages for the active compounds used according to the present invention are 200 mg. orally and 400 mg. rectally. For topical use, there is typically used a conventional carrier for this purpose containing 5% by weight of the active compound. A preferred form for oral administration is a gelatine capsule containing an aqueous alcoholic solution of the active compound and a similar form can be used for rectal administration.

We claim:

1. a method of treating inflammatory and pyretic conditions in mammals, including humans, which comprises administering an anti-inflammatory or antipyretic amount of an active compound of the formula:

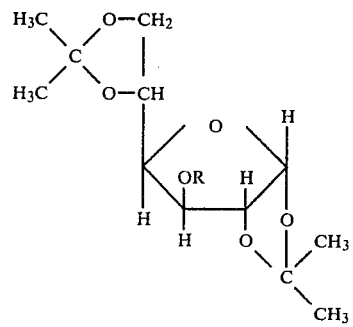

wherein R is a member selected from the group consisting of a straight-chained and branched alkyl radical contianing at least 5 carbon atoms, an alkenyl radical containing at least 4 carbon atoms, an alkynyl radical containing up to 6 carbon atoms, an acyloxy radical containing up to 6 carbon atoms, an alkoxy radical containing up to 6 carbon atoms, a carboxyalkyl radical containing up to 6 carbon atoms and a radical of the formula

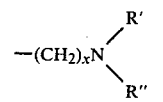

in which x is a whole number of up to 5 and R' and R" are each a member selected from the group consisting of a hydrogen atom and an alkyl radical containing up to 6 carbon atoms, or in which R' and R", together with the nitrogen atom to which they are attached, form a heterocyclic ring which can contain an additional heteroatom; or an acid-addition salt thereof when the active compound is basic, to a mammal requiring treatment for an inflammatory or pyretic condition.

* * * * *